US006440405B1

(12) United States Patent
Cooper et al.

(10) Patent No.: US 6,440,405 B1
(45) Date of Patent: Aug. 27, 2002

(54) QUATERNARY AMMONIUM FUNCTIONALIZED DENDRIMERS AND METHODS OF USE THEREFOR

(75) Inventors: Stuart L. Cooper, Chicago, IL (US); Chris Zhisheng Chen, Media, PA (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 09/588,585

(22) Filed: Jun. 6, 2000

Related U.S. Application Data

(60) Provisional application No. 60/137,927, filed on Jun. 7, 1999.

(51) Int. Cl.[7] .................. A61K 31/74; A61K 47/48; A61K 33/02; C07C 211/62
(52) U.S. Cl. ............. 424/78.17; 424/486; 424/719; 424/DIG. 16; 564/281
(58) Field of Search .................. 424/78.17, 450, 424/DIG. 16, 719, 486; 435/235.1; 528/176; 564/281

(56) References Cited

U.S. PATENT DOCUMENTS

| 4,631,337 A | * | 12/1986 | Tomalia et al. ............. 528/391 |
| 4,713,975 A | * | 12/1987 | Tomalia et al. ............ 73/865.8 |
| 5,962,423 A | | 10/1999 | Bundle et al. ................ 514/25 |
| 5,998,565 A | * | 12/1999 | de Brabander-van den Berg et al. ........................ 528/176 |
| 6,121,036 A | * | 9/2000 | Ghanbari et al. ......... 435/235.1 |
| 6,224,898 B1 | | 5/2001 | Balogh et al. |

FOREIGN PATENT DOCUMENTS

| WO | WO 98/06691 | 2/1998 |
| WO | WO 98/26662 | 6/1998 |

OTHER PUBLICATIONS

Chen et al., Book of Abstracts, 218th ACS National Meeting, Aug. 1999, PMSE–118.
O. Rahn and W. Eseltine, *Annual Review of Microbiology*, 1, 173–92 (1947).
H. Sommer, L. Jackson, *J. Org. Chem*, 35, 1558 (1970).
H. Sommer, H. Lipp, L. Jackson, *J. Org. Chem*, 36, 824 1971.
L. Donaruma, O. Vogl, "Polymeric Drugs", pp. 161–184, Academic Press: New York (1978).
"Disinfection, Sterilization, and Preservation", pp. 309–329, 3 ed., Lea and Febiger (1983).
"Anionic Polymeric Drugs", pp. 2–20, John Wiley & Sons: New York.
H. Yuan and S. Tazuke, *Polymer Journal*, 15, 125–133 (1983).
D. Tomalia, V. Berry, M. Hall, and D.M. Hedstrand, *Macromolecules*, 20, 1164–1167 (1987).
D. Tomalia, A. Naylor, and W. Goggard, *Agnew. Chem. Int. Ed. Engl.*, 29, 138–175 (1990).
C. Hawker and J.M.J. Frechet, *J. Am. Chem. Soc.*, 112, 7638–7647 (1990).
S. Denyer and Q. Hugo, "Mechanisms of Action of Chemical Biocides", pp. 331–334, Blackwell Scientific Publications: Oxford (1991).
M. Vaara, *Micobiol. Rev.*, 56, 395–411 (1992).
A. Kanazawa, T. Ikeda, and T. Endo, *Journal of Polymer Science*, 31, 335–343 (1993).
A. Kanazawa, T. Ikeda, and T. Endo, *Journal of Polymer Science*, 31, 1441–1447 (1993).
A. Kanazawa, T. Ikeda, and T. Endo, *Journal of Polymer Science*, 31, 1467–1472 (1993).
A. Kanazawa, T. Ikeda, and T. Endo, *Journal of Polymer Science*, 31, 3003–3011 (1993).
A. Kanazawa, T. Ikeda, and T. Endo, *Journal of Polymer Science*, 31, 3031–3038 (1993).
E. M.M. de Bradander–van den Berg and E.W. Meijer, *Agnew. Chem. Int. Ed. Engl.*, 32, 1308–1311 (1993).
J. Frechet, *Science*, 263, 1710–1715 (1994).
R. Roy, *Polymer News*, 21, 226–232 (1996).
G.R. Mewkome, C.N. Moorefield, F. Vogtle, "Dendritic Molecules Concepts Sytheses Perspectives", pp. 2–13, VCH: Weinheim, (1996).
D. Zanini and R. Roy, *J. Am. Chem. Soc.*, 119, 2088–2095 (1997).
H. Hansen, S. Haataja, J. Finne, and G. Magnusson, *J. Am. Chem. Soc.*, 119, 6974–6979 (1997).
M. Mammen. S. Choi, and G. Whitesides, *Agnew. Chem. Int. Ed. Engl.*, 37, 2754–2794 (1998).
Z. Chen, J. Oh, P. Dhurjati, T. Van Dyk, R. LaRossa, and S. Cooper, 24th Annual Meeting of the Society for Biomaterials, Apr. 22–26 San Diego, CA, (1998).
Z. Chen, N. Tan, and S. Cooper, *Chem Commun.*, 1585–1586 (1999).
H. Arimoto, K. Nishmura, T. Kinumi, I. Hayakawa, and D. Uemura, *Chem. Commun.*, (1999)
G. Newkome, E. He, and C. Moorefield, Chem. Rev., 99, 1689–1746 (1999).
L. Balogh, A. McManus, D. Tomalia, G. Hagnauer, American Chemical Society Division of Colloid and Surface Chemistry Abstracts, 218th ACS National Meeting, New Orleans, LA, Aug. 22–26 (1999).

\* cited by examiner

*Primary Examiner*—Thurman K. Page
*Assistant Examiner*—Blessing Fubara
(74) *Attorney, Agent, or Firm*—Connolly Bove Lodge & Hutz LLP

(57) ABSTRACT

Quaternary ammonium functionalized dendrimers are described which are suitable for controlling the growth of microorganisms. The quaternary ammonium functionalized dendrimer biocides of the present invention are effective against a wide variety of microbial species including bacteria, spores, yeast, fungi, mold and multicellular microorganisms.

28 Claims, No Drawings

QUATERNARY AMMONIUM FUNCTIONALIZED DENDRIMERS AND METHODS OF USE THEREFOR

Priority is claimed under 35 USC §119(e) from United States Provisional Application Ser. No. 60/137,927 filed Jun. 7, 1999; the entirety of which is herein incorporated by reference.

FIELD OF THE INVENTION

The present invention relates to quaternary ammonium functionalized dendrimers and methods of use therefor. Particularly, functionalized dendrimers comprised of Formula I are the object of the invention as well as their use as antimicrobial agents.

BACKGROUND OF THE INVENTION

Jacobs and coworkers first described the antimicrobial activity of many quaternary ammonium compounds (QACs) in 1915. Jacobs, W. A.; Heidelberger, M. *J. Biol. Chem.* 1915, 20, 659–683, 685–694; Jacobs, W. A.; Heidelberger, M. *J. Biol. Chem* 1915, 21, 103–143, 145–152, 403–407, 439–453, 455–464, 465–475. The second, and most important event in the development of quaternary ammonium biocides occurred in 1935 when Domagk reported that the antibacterial activity of long-chain quaternary ammonium salts was significantly more potent than their short chain counterparts. Domagk, G. *Deut. Med. Wochs.,* 61, 829 (1935). The markedly improved antimicrobial activity that occurred when a large aliphatic residue was attached to the quaternary nitrogen atom established the practicality and utility of these compounds, first in medicine, and later in many industrial applications. This important disclosure stimulated further research in synthesis and antimicrobial testing of QACs. It was shown that quaternary ammonium salts are most effective when one substituent is an alkyl chain with at least eight carbon atoms. Rahn, O.; Van Wseltine, W. *Annual Review of Microbiology* 1947, 1, 173. The issue of alkyl chain length was considered again when Cutler et al. studied how size affects the antimicrobial activity of a homologous series of alkyldimethylbenzyl ammonium chlorides. They found out that the highest potency is achieved when the alkyl chain has 14 carbons. Block, S. *Disinfection, Sterilization and Preservation;* 3rd ed.; Lea & Febiger: Philadelphia, 1983.

Quaternary ammonium compounds are currently widely used as disinfectants. They are surface-active, widespectrum antimicrobial agents. QACs are generally known to be more active against Gram-positive bacteria such as S. aureus than Gram-negative bacteria such as *E. coli.*

Literally hundreds to thousands of polymeric compounds have been prepared and tested for antimicrobial properties. However, very few polymer compounds with biological activity have been discovered. The only commercially important polymeric biocide is biguanide. Biguanides show a wide spectrum of antimicrobial activity and are much more potent than the related monomers. Davies, A., Bentley, M. Field, B. S. *J. Appl. Bacteriol.,* 31, 448–452 (1968).

Biofilms are matrix-enclosed bacterial populations adherent to each other and/or to surfaces or interfaces. Due to the destructive impact of biofilms in such diverse areas such as human physiology, food processing, and marine shipping, there is a great sense of urgency in the scientific community to discover chemical compositions and methods of use to solve biofilm-related problems.

Biofilms in human physiology can withstand host immune responses and are resistant to antibiotics. Antibiotics have proven to be ineffective in the prevention and treatment of biofihm infections particularly associated with biomaterial implants and prosthetic devices. Costerton, et al., *Behaviour of Bacteria in Bioflims,* ASM News, 55(12):650 (1989); AnWar, et al., *Effective Use of Antibiotics in the Treatment of Biofilm-Associated Infections,* ASM News, 58(12):665 (1992). Biofilm infections can occur either on dead/inanimate surfaces, such as sequestra of dead bone and medical devices, or on living tissues, as in the case of endocarditis. Biofilms grow very slowly; however, they are rarely resolved by any host defense system, even for those individuals with excellent immune systems. Bacterial colonization on implanted medical devices such as indwelling catheters, cardiac pacemakers, prosthetic heart valves, chronic ambulatory peritoneal dialysis catheters, and prosthetic joints, and the subsequent transformation into invasive infections contribute significantly to morbidity and complications related to implant-centered infections. Clinical studies have shown that even one thousand times the concentration of antibiotic that would typically kill planktonic (free-floating) bacteria fails to kill bacteria aggregated in the form of a biofilm. Costerton, et al., *Annu. Rev. Microbiol.,* 49, 711–745 (1995); Costerton, J. W. *J. Ind. Microbiol.,* 15, 137–140 (1995).

Biofilm bacteria are moreover resistant to bacteriophage and to a wide variety of antimicrobial agents used to combat biofouling in industrial environments.

Food processing, for example, can lead to food poisoning through such bacteria as, for example, Salmonella species, *Clostridium perfringens,* Bacillus species, *Staphylococcus aureus,* and *Escherichia coli.* Standard concentrations of various food processing industry standard disinfectants to clean surfaces in the industry is often ineffective thereby contributing to the public health risk factor. Walker, et al., *Colloids & Surface A,* 77, 225–229 (1993).

Biological fouling in the marine environment occurs on a variety of surfaces, including ships hulls, oil and gas installations and piers. Fouling on static structures increases loading forces caused by waves and currents on supports, and impedes inspection and maintenance. Biofilms in tubes and pipes can increase pressure drop and cause clogging. Biofouling on ships reduces their speed and maneuverability, due to the increased drag introduced by biological accumulations, causing increased fuel consumption and maintenance costs. Current marine anti-fouling technology employs biocides such as organotins which are blended into coatings as a preventive measure against growth of microorganisms. However, the ships treated in this manner require the arduous task of relatively frequent treatment. There is considerable interest in developing engineering approaches to modify susceptible surfaces to prevent biofilm formation. Several approaches have been actively investigated including modifying surfaces to minimize bacterial attachment or bacterial growth control through antimicrobial agents. Currently available approaches have not presented a formula for success. Moreover, traditional antibiological warfare agents are known to be very reactive and extremely toxic. Such agents include chlorine, formaldehyde, and peroxygen to destroy and or neutralize the effect of Anthrax spores and other biological entities. Accordingly, there also exists a need for antibiological warfare agents that are nonreactive and are virtually nontoxic to human skin.

Because of their compact structure and the availability of many end groups, dendrimers have attracted attention as possible antimicrobial agents. Zanini et al, Schengrund et al, and Bundle, et al. investigated carbohydrate modified dendrimers as antibacterial agents and using these oligosaccharides for treating and preventing bacterial and viral disease. Zanini, D.; Roy, R. *J. Am. Chem. Soc.,* 119, 2088–2095 (1997); Roy, et al, *J. Chem. Soc. Chem. Commun.,* 1869–1872 (1993); Schengrund et al, WO patent 9826662, 1998; U.S. Pat. No. 5,962,423, 1999. All these investigators took advantage of the multiple end groups of dendrimers and introduced different carbohydrates onto the dendrimers. These modified dendrimers tend to enhance the carbohydrate-protein binding interactions and can be potent inhibitors for bacterial and viral infections. The carbohydrate chemistry utilizes the specific interaction of a the carbohydrate with the bacteria. The use of these specific interactions limit the application of these carbohydrate dendrimers since different bacteria only respond to different carbohydrates. The quaternary ammonium functionalized dendrimers of the current invention use non-specific interactions with the bacteria and are therefore effective against a wide range of bacteria, spores, yeast, fungi, and mold. Balogh et al. synthesized dendrimer nanocomposites, dendrimers with inorganic silver or silver ions, and tested their antibacterial properties. Balogh, L. *Proc. Am. Chem. Soc. Div. Colloi. & Surf. Chem.,* 54. (1999). For these dendrimer nanocomposites, the dendrimer itself does not have any antibacterial property. The activity comes from the silver/ silver ions. In contrast, the quaternary ammonium functionalized dendrimers of the current invention derive antibacterial properties from the dendrimer itself. The dendrimers of the current invention are different from all previous investigations in that the surface groups of the dendrimers were transformed into quaternary ammonium groups. Unlike known QACs, the quaternary ammonium functionalized dendrimers of the current invention are more effective against Grain-negative bacteria such as *E. coli.*

SUMMARY OF THE INVENTION

A quaternary ammonium functionalized dendrimer of Formula I is provided:

$$D_n\text{---}(R\text{---}\underset{\underset{B}{|}}{\overset{\overset{A}{|}}{N^+}}\text{---}Y)_z \quad X^-$$

(Formula I)

wherein wherein D is a dendrimer; n is the generation number of the functionalized dendrimer; z is an integer less than or equal to $2^{(n+1)}$; x is an anion; R is a linking group; Y is an alkyl group or aryl group; A is an alkyl group or aryl group, and B is an alkyl group or aryl group.

Methods of using the functionalized dendrimers of Formula I as effective broad spectrum antimicrobial agents in the healthcare as well as in various industrial applications are also provided.

DETAILED DESCRIPTION OF THE INVENTION

Unless defined otherwise, all technical and scientific terms used herein have the same meaning as is commonly understood by one of skill in the art to which this invention belongs. All publications and patents referred to herein are incorporated by reference.

Controlling the growth of a microrganism as used herein is intended to encompass effecting diminished proliferation and/or lethal results to microorganisms including but not limited to bacteria, spores, yeast, fungi, mold and multicellular microorganisms. Microorganisms listed in Table I are particularly preferred. The functionalized dendrimers of the current invention are particularly intended to be employed in connection with each of the materials, tissues and sites recited in Table I. A spore as used herein refers to various small or minute primitive reproductive bodies, or resistant resting cells, typically unicellular. Also refers to the dustlike asexual reproductive bodies of fungi. A spore can for example corresponds to *B. anthracis* or anthrax.

Exposing a microorganism to a quaternary ammonium functionalized dendrimer of the present invention as used herein is intended to encompass subjecting a microorganism to sufficient proximity to a functionalized dendrimer of the present invention to cause an effect in the growth or proliferation of one or more microorganisms including but not limited to physical interaction between the microorganism and the functionalized dendrimer. This is intended to encompass exposure/interactions in solution as well as solid phase exposure/interaction, and liquid/solid phase exposure.

For example, liquid/solid phase exposure of the quaternary ammonium functionalized dendrimer of the present invention to one or more microorganims may involve using the quaternary ammonium functionalized dendrimer in a spray mixed with a suitable liquid carrier. Spray as used herein refers to the quaternary ammonium functionalized dendrimer of the present invention with or without a suitable carrier liquid applied as a liquid stream, fine vapor, mist, small drops, aerosol, or non-aersol. This spray can then be used to expose a microorganism to a quaternary ammonium functionalized dendrimer in liquid form. The spray could be used for example to control the growth of a microorganisms in or on clothing and surfaces.

The functionalized dendrimers are also intended for industrial as well as medical and home use applications including but not limited to elements of protective coatings such as paints, handwash formulations, means for use in ointments and related topical applications, cosmetics, cleaning and/or disinfectant/sanitation products, and sanitation of recreational water such as swimming pools and spas. The functionalized dendrimers are also intended to be used as a component in coating fibers and filters. The functionalized dendrimers are also effective against Anthrax spore. The dendrimer biocides of the present invention are nonreactive and are virtually nontoxic to human skin.

The functionalized dendrimers can also be immobilized on the surface of materials to create efficient antimicrobial environments in a wide variety of applications including garments for protective use as well as biomaterials and prosthetic devices for medical use. For example quaternary ammonium functionalized dendrimer of the present invention can be immobilized to polymers, glass, and metals. Polymers can be for example polyurethanes. Other examples include polystyrene, rubber, polyethylene, polypropylene, and engineering plastics. Immobilized on the surface is defined as attachment of functionalized dendrimers to a surface by covalent bonding, ionic interaction, coulombic interaction, hydrogen bonding, crosslinking (e.g., as crosslinked (cured) networks) or as interpenetrating networks, for example.

A method of controlling the growth of a microorganisms is herein provided comprising exposing a microorganism to a quaternary ammonium functionalized dendrimer of the present invention. Functionalized dendrimers of the present invention may be employed in solution (or initially in solution which may dessicate or carrier solvent may evaporate for example for coatings, paint and the like) at an effective concentration to control the growth of microorganisms. The functionalized dendrimers of the present invention may be employed at a wide variety of concentrations. Concentration of up to 100% may be used. Otherwise functionalized dendrimer of the present invention can be effective at concentrations from 1 ppm to concentration in excess of 10%. Effective minimum concentrations of functionalized dendrimers of the present invention against common bacteria is contemplated to be in concentrations 5 ppm to 1 to 2%. Preferred concentration is from 10 ppm to 200 ppm. More preferred is 20 ppm to 100 ppm. The concentration depending upon the role at hand (e.g., employment as a pre-surgical handwash disinfectant, coating for a biomaterial or otherwise prosthetic device for internal use, or element of an industrial-use biocidal coating). Elements for the formulations of functionalized dendrimers described herein are well known and are described, for example, in U.S. Pat. Nos. 6,030,632, 5,869,073, 6,022,551; 5,906,808; 5,776,430; 5,597,561; 5,244,666; and 5,164,107, each of which is herein incorporated by reference.

Table I is a partial list of infections. Quaternary ammonium functionalized dendrimers provided herein are contemplated to be effective against these and other bacterial species as well as spores, mold, fungi and other multicellular microorganisms.

TABLE I

Partial list of infections

| Infection or disease | Common bacterial species Human disease |
|---|---|
| Dental caries | Acidogenic Gram-positive cocci (e.g. Streptococcus) |
| Periodontitis | Gram-negative anaerobic oral bacteria |
| Otitis media | Nontypable strains of Haemophilus influenzae |
| Musculoskeletal infections | Gram-positive cocci (e.g. *staphylococci*) |
| Necrotizing fasciitis | Group A streptococci |
| Biliary tract infection | Enteric bacteria (e.g. *Escherichia coli*) |
| Osteomyelitis | Various bacterial and fungal species--often mixed |
| Native valve endocarditis | Viridans group streptococci |
| Cystic fibrosis pneumonia | *P. aeruginosa* and *Burkholderia cepacia* |
| Meloidosis | *Pseudomonas pseudomallei* |
| | Medical device related infection |
| ICU pneumonia | Gram-negative rods |
| Sutures | *Staphylococcus epidermidis* and *S. aureus* |
| Exit sites | *S. epidermidis* and *S. aureus* |
| Arteriovenous shunts | *S. epidermidis* and *S. aureus* |
| Schleral buckles | Gram-positive cocci |
| Contact lens | *P aeruginosa* and Gram-positive cocci |
| Urinary catheter cystitis | *E. coli* and other Gram-negative rods |
| Peritoneal dialysis peritonitis | A variety of bacteria and fungi |
| Endotracheal tubes | A variety of bacteria and fungi |
| Hickman catheters | *S epidermidis* and *C. albicans* |
| Central venous catheters | *S. epidermidis* and others |
| Mechanical heart valves | *S. aureus* and *S. epidermidis* |
| Vascular grafts | Gram-positive cocci |
| Biliary stent blockage | A variety of enteric bacteria and fungi |
| Orthopedic devices | *S. aureus* and *S. epidermidis* |

Anthrax is a typical biological weapon. Novel quaternary ammonium functionalized dendrimers of the current invention can denature Anthrax spore, such as avirulent *B. anthracis* spore. The quaternary ammonium functionalized dendrimer biocides can be used as a denaturing spray or be impregnated in a soldiers uniform. Table II shows the denaturing effect of quaternary ammonium functionalized dendrimer biocides on Avirulent *B. anthracis* spore.

TABLE II

Denaturing effect of quaternary ammonium functionalized dendrimer biocides on Avirulent B. anthracis spore.

| Dendrimer Concentration | % Viable Spores | | |
|---|---|---|---|
| | D5ClNC12 | D3ClNC12 | D1ClNC12 |
| .20% | 9.5 | 50.2 | 2.0 |
| .10% | 8.4 | 68.6 | 4.4 |
| .05% | 14.2 | 60.1 | 7.5 |
| .01% | 94.8 | 64.6 | 36.1 |

The margin of error is 5–8% for the % of viable spores. The concentration of the Avirulent B. anthracis spore was $10^7$ spores per ml. The contact time was 1 hour. Functionalized dendrimers of the present invention are moreover contemplated to provide effective protection against biological warfare agents such as anthrax. Embodiments which employ functionalized dendrimers of the present invention accordingly include a denaturing spray or protective clothing impregnated with functionalized dendrimers as described herein. Effectiveness against anthrax spore is contemplated to be in concentrations from 0.1% to 20%. Preferred concentration is from 1% to 10%.

R as used herein refers to a linking group to link the quaternary ammonium group to the surface group of the Dendrimer (D). The linking group R can be either rigid or flexible. The linking group R can be for example an alkyl or aryl group. R may preferably selected from the group consisting essentially of —CO—NH—CH2—CH2—, —CO—NH—CH2—, —CO—NH—CH2—CH2—CH2—, —CO—NH—CH2—CH2—CH2—CH2, —CO—NH—CH2—CH2—CH2—CH2—CH2—, —CO—NH-Phenyl-CH2—, —CO—NH—CH2—CH2—O—CH2—CH2—, —(CH2)—, —(CH2)$_2$—, —(CH2)$_3$—, —(CH2)$_4$—, —(CH2)$_5$—, —(CH2)$_6$—, —(CH2)$_7$—, —(CH2)$_8$—, —(CH2)$_9$—, —(CH2)$_{10}$—, —(CH2)$_{11}$—, —(CH2)$_{12}$—, —(CH2)$_{13}$—, —(CH2)$_{14}$—, —(CH2)$_{15}$—, —(CH2)$_{16}$—, —(CH2)$_{17}$—, —(CH2)$_{18}$—, —(CH2)$_{19}$—, and —(CH2)$_{20}$— as well as similar physiochemical structures. The linking group is at least one carbon atom in length, and may be C1–20 straight, branched or cyclic alkyls, in which one or more of the carbons may be replaced with an O, S, or N.

Y, A, or B Alkyl group or aryl groups as used herein refers to chemical entities having less than 40 carbon atoms. Y, A, and/or B may also be chloromethyl.

Dendrimers are well defined, highly branched macromolecules that emanate from a central core. Commercially available dendrimers include polyamidoamine (PAMAM) dendrimers and polypropylene imine (PPI) dendrimers. Dendriditic architecture brings a very high number of functional groups in a compact space. Dendrimers in the present invention can for example be selected from the group consisting of polyamidoamine dendrimers, polylysine based dendrimers, polyethylene oxide based dendrimers, silicon based dendrimers, polyether based dendrimer and polypropylene imine dendrimers. A polylysine based dendrimers refers to a dendrimer in which the backbone or structure consists essentially of polylysine. A polyethylene oxide based dendrimers refers to a dendrimer in which the backbone or structure consists essentially of polyethylene oxide. A silicon based dendrimers refers to a dendrimer in which the backbone or structure consists essentially of silicon. A polyether based dendrimer refers to a dendrimer in which the backbone or structure consists essentially of polyether.

Architecturally similar to dendrimers, hyperbranched polymers can be prepared using a one-pot synthesis, so they are typically polydisperse, structurally imperfect, and better positioned for industrial applications. Hyperbranched polymers can be for example polyethylene oxide based hyperbranched polymers, polyglycerol based hyperbranched polymer and silicon based hyperbranched polymers. A polyethylene oxide based hyperbranched polymer refers to a hyperbranched polymer in which the backbone or structure consists essentially of polyethylene oxide. A polyglycerol based hyperbranched polymer refers to a hyperbranched polymer in which the backbone or structure consists essentially of polyglycerol. A silicon based hyperbranched polymer refers to a hyperbranched polymer in which the backbone or structure consists essentially of silicon. Commercially available Hyperbranched polymers include Polyols from Perstop Inc. which is an example of a hyperbranched polyols and hybrane™ from DSM. Hybrane as used herein refers to the commercially available hybrane™ from DSM.

D as used herein refers to dendrimers that are highly branched macromolecules that emanate from a central core as well as hyperbranched polymers. When used in relation to the letter D, the word dendrimer refers to both conventional dendrimers that emanate from a central core as well as hyperbranched polymers. D can be selected for example from the group consisting essentially of polyamidoamine, polylysine based dendrimers, polyethylene oxide based dendrimers, silicon based dendrimers, polypropylene imine dendrimers, polyether dendrimers, polyethylene oxide based hyperbranched polymers, polyglycerol based hyperbranched polymers, silicon based hyperbranched polymers, hyperbranched polyols and hybrane™ from DSM.(Geleen, Netherlands).

N as used in Formula I is nitrogen.

Through a series of reaction and purification steps, dendrimers grow radially outwards. At different stages of the synthesis, dendrimers are identified by generations. As the generation increases, the number of surface groups, the size of the dendrimer, and the molecular weight of the dendrimer increase.

The variable "n" as used herein refers to the generation of the Dendrimer D. Therefore $D_1$, $D_2$ or $D_3$ represent dendrimers of generation 1, 2, and 3 respectively The variable "z" as used herein refers to the number of surface functional groups for a dendrimer. As the generation, n, of any dendrimer increases, the number of surface functional groups, z, increases. A generation 1 dendrimer, $D_1$, may have as many as many as four surface functional groups, while a generation 2 dendrimer, $D_2$, may have a many as eight surface functional groups. The maximum number of functional groups is represented by the letter z when it is equal to $2^{n+1}$ where n is equal to generation of a given dendrimer. Because a given dendrimer may have less than the maximum number of possible surface groups functionalized, the actual number of functionalized groups on a given dendrimer is less than or equal to $2^{n+1}$.

The variable "x" as used herein refers to an anion. The variable element of the invention x is preferably selected from, but not limited to chloride, bromide, sulfate, nitrate, chlorate, tetrafluoroborate, perchlorate, hexafluorophosphate, permanganate, sulfite.

The advent of dendrimers represents a major breakthrough in synthetic chemistry. Dendrimers can be tailored to generate uniform or discrete functionalities and possess tunable inner cavities, surface moieties, sizes, molecular weights, and solvent interactions. Dendrimers can be synthesized by a convergent approach. Tomalia, et al. *Macromolecules,* 20, 1164. (1987). Dendrimers can also be synthesized by a divergent approach. Tang, et al. *Bioconjugate Chem.,* 7, 703–714. (1996). In the divergent approach, growth of dendrimers dendrimers starts from a multifunctional core. Through a series of reaction and purification steps, dendrimers grow radially outwards. At different stages of the synthesis, dendrimers are identified by generations. As the generation increases, the number of functional groups, the size of the dendrimer, and the molecular weight of the dendrimer increase. At a certain stage of the synthesis, steric hindrance prevents one from achieving the, where the highest generation is synthesized. Commercially available dendrimers, such as polyamidoamine (PAAM) dendrimers from Dendritech Inc. (Midland, Mich., USA) and polypropylene imine (PPI) dendrimers from DSM (Geleen, Netherlands) are synthesized by the divergent approach. In the convergent approach, dendrons, as parts of dendrimers, are synthesized according to the divergent approach and these dendrons are then coupled to a multifunctional core. The advantage of the convergent approach is that the chemistry of each dendron can be different, and distinct functional groups can be integrated into dendrimers at precise sites. Due to the repetitive nature of the dendrimer synthesis and the extensive purification required to achieve the, dendrimers are very expensive and not readily available. The combination of discrete numbers of functionalities in one molecule and high local densities of active groups has attracted a lot of attention, especially for biological applications. The unique architecture of dendrimers, they have been investigated for a wide variety of applications, such as gene delivery vesicles, Tang, et al., *Bioconjugate Chem.* 7, 703–714 (1996); Kukowska-Latallo, et al., *Proc. Natl. Acad. Sci. USA,* 93, 4897–4902 (1996), catalysts, Zeng, F. Z., S. C. *Chem. Rev.,* 97, 1681 (1997); Newkome, et al., *Chem. Rev.,* 99, 1689–1746 (1999), drug delivery carriers, Liu, M.; Frechet, J. M. *J. Proc. Am. Chem. Soc. Polym. Mater. Sci. Engr.,* 80, 167 (1999); Uhrich, K. *TRIP,* 5, 388–393 (1997); Liu, H.; Uhrich, K. *Proc. Am. Chem. Soc. Div. Polym. Chem.,* 38, 1226 (1997), chromatography stationary phases, Matthews, et al., *Prog. Polym. Sci.,* 23, 1–56 (1998), boron neutron capture therapy agents, Newkome, et al., *Dendritic Macromolecules: Concepts, Syntheses, Perspectives;* VCH: Weinheim, Germany, (1996); Newkome, G. R. *Advances in Dendritic Macromolecules;* JAI Press: Greenwich, Conn., Vol. 2. (1995), and magnetic resonance imaging contrast agents. Tomalia, D. A. *Adv. Mater.,* 6, 529–539. (1994).

Dendrimers can offer a high local concentration of functional groups. A functionalized dendrimer is a dendrimer with surface groups that have been replaced with a chemical functional group. A surface groups is the chemical groups at the terminal ends of the branches or backbone of a dendrimer. Surface groups can be for example —NH2, —OH, —COOH, —CN. For example a polypropylene imine (PPI) dendrimer is terminated with —NH2 surface groups. Chemical groups can be added to these surface groups such the resulting dendrimer is terminated by a —NH—W group wherein W is some functional chemical group. Functionalized dendrimers with biologically active groups, results in an increased potency associated with the high local concentration. Once a dendrimer has been functionalized, they may be called functionalized dendrimers or modified dendrimers. The resulting functionalized dendrimer can be represented by Dn-(W)z. The dendrimer can be referred to through use of "D" to refer to the dendrimer structure except for the chemical functional group represented by W. The generation of the dendrimer D can be represented by the letter n. The letter "n" a defined herein represents the generation of the Dendrimer D. Therefore $D_1$, $D_2$ or $D_3$ represent dendrimers of generation 1, 2, and 3 respectively. As the generation of any dendrimer increases, the number of potential surface functional groups, z, increases. A generation 1 dendrimer, $D_1$, may have as many as four surface functional groups, while a generation 2 dendrimer, $D_2$, may have a many as eight surface functional groups. The maximum number of functional groups, is represented by the letter z, when it is equal to $2^{n+1}$ where n is equal to generation of a given dendrimer. Because a given dendrimer may have less than the maximum number of possible surface groups functionalized, the actual number of functionalized groups on a given dendrimer is less than or equal to $2^{n+1}$. During formation of the dendrimer biocide system, precipitation may be observed during the reaction, resulting in incomplete reaction and inhomogeneity of the dendrimer biocides. This results in the actual number z being variable across dendrimer biocides.

Quaternary ammonium compounds are currently widely used as disinfectants. A quaternary ammonium functionalized dendrimers is a functionalized dendrimer can be represented by Dn-(W)z wherein the chemical structure of the chemical group W is terminated by a quaternary ammonium compound.

Generally speaking, biocides immobilized on dendrimers can be more effective if the target sites are cell walls and/or cell membranes. Since there are many QACs on the dendrimer, the resulting dendrimer biocides are polycationic. Polycationic structure has been proven to improve the permeability of the bacterial membrane and facilitate the antimicrobial action of biocides. Antimicrobial functionalities may be placed onto dendrimers and used to combat microbial fouling/infections. Another complementary approach is to prevent the initial attachment of bacteria to surfaces. The attachment is usually a prerequisite for colonization of bacteria and invasion of tissues.

Quaternary ammonium functionalized dendrimers provided herein outperform known polymeric and small molecule biocides. The dendrimer architecture has been shown to be over 100 times more potent against E. coli as compared to their small molecule counterparts such as n-dodcecyltrimethyl ammonium chloride (DTAC). Small molecule QACs are not very effective on Gram-negative bacteria, such as E. coli, because these cells have very sophisticated outer membrane structures that effectively keep out antibacterial agents. However. with the combination of the high functional group density and the increased permeability due to the polycationic structure, dendrimer reach and disrupt cell membranes, eventually leading to cell death. Functionalized dendrimers comprised of Formula I can be used in any of a myriad of applications that requires a potent biocide/antimicrobial agent. Particularly the present invention is drawn toward quaternary ammonium functionalized dendrimers comprised of Formula I which effect a very high number of functional groups in a compact space and therefore increase local concentration of biocidal agents.

Quaternary ammonium functionalized dendrimers of the Formula I are subject of the current invention.

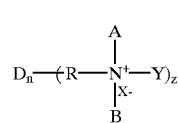

(Formula I)

A quaternary ammonium functionalized dendrimer of Formula I is provided: wherein D is a dendrimer; n is the generation number of the functionalized dendrimer; z is an integer less than or equal to $2^{(n+1)}$; x is an anion; R is a linking group; Y is an alkyl group or aryl group; A is an alkyl group or aryl group, and B is an alkyl group or aryl group. Alkyls can be linear or branched. The groups A, B, and Y can all be the same or may all be different. Quaternary ammonium functionalized dendrimer according are preferred wherein D is selected from the group consisting essentially of polyamidoamine, polylysine based dendrimers, polyethylene oxide based dendrimers, silicon based dendrimers, polypropylene imine dendrimers, polyether dendrimers, polyethylene oxide based hyperbranched polymers, polyglycerol based hyperbranched polymers and silicon based hyperbranched polymers. Dendrimers of the current invention are preferred wherein n ranges from 1 to 15, 1–6 being most preferred. x represents an anion. The variable element of the invention x is preferably selected from, but not limited to chloride, bromide, sulfate, nitrate, chlorate, tetrafluoroborate, perchlorate, hexafluorophosphate, permanganate, sulfite. Linking group R may preferably selected from the group consisting essentially of —CO—NH—CH2—CH2—, —CO—NH—CH2—, —CO—NH—CH2—CH2—CH2—, —CO—NH—CH2—CH2—CH2—CH2, —CO—NH—CH2—CH2—CH2—CH2—CH2—, —CO—NH-Phenyl-CH2—, —CO—NH—CH2—CH2—O—CH2—CH2—, —(CH2)—, —(CH2)$_2$—, —(CH2)$_3$—, —(CH2)$_4$—, —(CH2)$_5$—, —(CH2)$_6$—, —(CH2)$_7$—, —(CH2)$_8$—, —(CH2)$_9$—, (CH2)$_{10}$—, —(CH2)$_{11}$—, —(CH2)$_{12}$—, —(CH2)$_{13}$—, —(CH2)$_{14}$—, —(CH2)$_{15}$—, —(CH2)16—, —(CH2)$_{17}$—, —(CH2)$_{18}$—, —(CH2)$_{19}$—, and —(CH2)$_{20}$—, as well as similar physiochemical structures. Y is preferably an alkyl or aryl group consisting of within the range of 1 to 32 carbon atoms. Y may be linear or branched. Y may be an alkyl group consisting of within the range of 1 to 32 carbon atoms. Y is preferably a linear alkyl group consisting of within the range of 8 to 24 carbon atoms. Y may be an aryl group selected-from the group consisting essentially of phenyl, —(CH2)-phenyl, —(CH2)$_2$-phenyl, —(CH2)$_3$-phenyl, —(CH2)$_4$-phenyl, —(CH2)$_5$-phenyl, (CH2)$_6$-phenyl, —(CH2)$_7$-phenyl, —(CH2)$_8$-phenyl, —(CH2)$_9$-phenyl, (CH2)$_{10}$-phenyl, —(CH2)$_{11}$-phenyl, —(CH2)$_{12}$-phenyl, —(CH2)$_{13}$-phenyl, —(CH2)$_{14}$-phenyl, —(CH2)$_{15}$-phenyl, —(CH2)$_{16}$-phenyl, —(CH2)$_{17}$-phenyl, —(CH2)$_{18}$-phenyl, —(CH2)$_{19}$-phenyl, —(CH2)$_{20}$-phenyl, —(CH2)$_{21}$-phenyl, —(CH2)$_{22}$-phenyl, —(CH2)$_{23}$-phenyl, and —(CH2)$_{24}$-phenyl. Y may also be chloromethyl. A and B are alkyl or aryl groups, the same or different, each consisting of within the range of 1 to 32 carbon atoms. A and B can be liner or branched. A and B are preferably alkyl groups, the same or different, each consisting of within the range of 1 to 24 carbon atoms. A and B are most preferably linear alkyl groups, the same or different, each consisting of within the range of 1 to 24 carbon atoms; however, A and/or B may be an aryl group selected from the group consisting essentially of phenyl, —(CH2)-phenyl, —(CH2)$_2$-phenyl, —(CH2)$_3$-phenyl, —(CH2)$_4$-phenyl, —(CH2)$_5$-phenyl, —(CH2)$_6$-phenyl, —(CH2)$_7$phenyl, —(CH2)$_8$-phenyl, —(CH2)$_9$-phenyl, (CH2)$_{10}$-phenyl, —(CH2)$_{11}$-phenyl, —(CH2)$_{12}$-phenyl, —(CH2)$_{13}$-phenyl, —(CH2)$_{14}$-phenyl, —(CH2)$_{15}$-phenyl, —(CH2)$_{16}$-phenyl, —(CH2)$_{17}$-phenyl, —(CH2)$_{18}$-phenyl, —(CH2)$_{19}$-phenyl, —(CH2)$_{20}$-phenyl, —(CH2)$_{21}$-phenyl, —(CH2)$_{22}$-phenyl, —(CH2)$_{23}$-phenyl, and —(CH2)$_{24}$-phenyl. A and/or B may also be chloromethyl. Quaternary ammonium functionalized dendrimers of Formula I is preferred wherein D is an NH2 terminated polypropylene imine (PPI) dendrimer and n is from generation 1 to 6 and wherein R is —CO—NH—

CH2—CH2— and x is Chloride; or R is —CO—NH—CH2— and x is Bromide. Quaternary ammonium functionalized dendrimer are preferred wherein Y is preferably a linear alkyl group consisting of within the range of 8 to 24 carbon atoms. Functionalized dendrimers of the invention are particularly preferred wherein A and B are —CH3.

Quaternary ammonium compounds are usually synthesized by the addition of an alkyl halide to a tertiary amine. Davis, B., *Recent Developments in the Technology of Surfactants;* Porter, M. R., Ed.; Elservier Applied Sciences: London, ppp 70 (1990). This reaction is reversible at high temperature, so 30–80° C. is typically used for the synthesis. The quaternary ammonium salts are nearly insoluble in diethyl ether and benzene, sparingly soluble in acetone, and freely soluble in water and alcohol.

Five generations, for example, of poly(propylene imine) (PPI) dendrimers , D, with 4–64 primary amine surface groups, z, have been used to synthesize dendritic biocides. The functionalization of dendrimers consists of two steps. The first involves introducing halogen, such as chlorine or bromine, functionality to the dendrimer by reacting primary amine groups of the dendrimer with a bifunctional chemical such as 2-chloroethyl isocyanate or 2-bromoethyl isocyanate. The halogen can then react with tertiary amines to form quaternary ammonium compounds and with phosphines to form quaternary phosphonium salts. A homologous series of tertiary amines with the alkyl chain ranging from C8 to C16. Five times excess of the amine is typically used to facilitate the reaction and to prevent intra-dendrimer quaternization. The final products are usually obtained as yellow powders. For dendrimer biocides that were used in polyurethane functionalization, the chemistry is similar. However, the stoichiometry was adjusted so that there were still some free pendent halide groups left for the immobilization chemistry. In practice, usually only 80–90% of stoichiometric amount of tertiary amine is used.

For the reaction of the primary amine terminated dendrimer with 2-bromoethyl or 2-chloroethyl isocyanate, the reaction itself is very fast and can finish in seconds. Since the reaction is exothermic, cross-linking can happen if the heat is not properly removed. Therefore, the isocyanate may be added dropwise into the dendrimer solution. An ice bath may be used to lower the reaction temperature. There is not any limit in choosing solvents as long as the isocyanate-modified dendrimers are soluble in the solvent.

The reaction of a tertiary amine and the modified dendrimer finally results in a dendrimer biocide. The reaction rate can be enhanced in polar solvents such as DMF. Elevated temperature also improves the reaction rate; however, high temperature also leads to the reverse reaction, the degradation of quaternary ammonium compounds. The reaction can be conducted in several solvents. The reaction rate is in the order of DMF>1-butanol>acetone. Sommer and co-workers also found similar rate dependence on solvent and that the relative quaternization rate in various solvents is 900:285:70:1 (DMF:methanol:butanol:hexane). Sommer et al., *J. Org. Chem.*, 26, 824–828 (1971).

Compared to conventional polymers, the end groups of dendrimers play a more important role in determining their solubility. For example, the hydrophobically modified dendrimers, no matter what the interior structure of the dendrimers is, are soluble in hydrocarbons such as hexane and toluene. The solubility is primarily determined by the alkyl chain on the surface. Therefore, surface modification can lead to a significant difference in the solubility of the dendrimers. An appropriate solvent or solvent mixture must be selected if complete modification of the dendrimers is desirable. For the dendrimer biocide system, if DMF is used alone, precipitation may be observed during the reaction, resulting in incomplete reaction and inhomogeneity of the dendrimer biocides. Since the dendrimer gets more and more hydrophobic with the process of the reaction, addition of toluene to accommodate the hydrophobic part is required. Typically a 2:1 ratio of DMF:toluene mixture may be used for the quaternization reaction. The ratio can only be determined empirically and depends on the amount of the tertiary amine used in the reaction.

After the reaction, quaternary ammonium salts are repeatedly precipitated in large volumes of acetone. These precipitates are extremely hygroscopic. The precipitates is filtered, redissolved in a minimal amount of ethanol, and repeatedly stripped with anhydrous toluene to remove moisture. The samples are dried for ~120 hr at 65° C. in a vacuum oven and stored in a vacuum desiccator. Some samples appeared to be crystalline while others were amorphous. For the amorphous samples, recrystallization in acetone:methanol (9:1, v/v) improved sample purity.

These dendrimer biocides have a strong tendency to trap some excess tertiary amine and solvent. To further purify the samples, dialysis or diafiltration with a membrane with a 1000–2000 cut-off molecular weight is required. The dialysis process is typically very slow. A semi-continuous process called diafiltration, a combination of dialysis and ultrafiltration, may be used for purification. The diafiltration usually takes 2–3 days. The diafiltration may be stopped when the exit stream does not contain any tertiary amine or other small molecules detectable by a gas chromatography-mass spectrometer (GC-MS). The dendrimer biocides are also highly hygroscopic. Therefore, storage in vacuum desiccator is required.

The versatile chemistry allows for the preparation of a series of dendrimer biocides with different hydrophobes by using different tertiary amines, with different molecular weight, size and number of functional groups by using different generations of dendrimers, and with different counter-anions by using different isocyanates such as 2-bromoethyl isocyanate. These dendrimerbiocides are soluble in alcohol, chloroform, and dimethylformamide; slightly soluble in water; and not soluble in tetrahydrofuran, toluene, and acetone.

Table III represents potential dendrimers based on poly(propylene imine) (PPI) dendrimers. For the purposes of the following discussion and table a shorthand of DnXNY based on Formula 1 is used. Where D is a poly(propylene imine) (PPI) dendrimers if generation n. Having an anion X and Y group. When using the preceding nomenclature, groups A and B of formula are both —CH3, and the linking group, R, is represented by —NH—CONHCH2CH2— when the anion is chloride (Cl) and —NH—CONHCH2— when the anion is Bromide (Br). Therefore D1ClNC12 is a generation 1 poly(propylene imine) (PPI) with a chloride anion and Y group represented by an alkyl C12.

TABLE III

Example Functionalized Dendrimers

| | Generation (n) | Y | X | Max No. Functional Groups (z) | Theoretical MW |
|---|---|---|---|---|---|
| D1ClNC12 | 1 | C12 | Cl | 4 | 1593 |
| D2ClNC12 | 2 | C12 | Cl | 8 | 3324 |

TABLE III-continued

Example Functionalized Dendrimers

| | Generation (n) | Y | X | Max No. Functional Groups (z) | Theoretical MW |
|---|---|---|---|---|---|
| D3ClNC12 | 3 | C12 | Cl | 16 | 6789 |
| D4ClNC12 | 4 | C12 | Cl | 32 | 13719 |
| D5ClNC12 | 5 | C12 | Cl | 64 | 27578 |
| D2ClNC16 | 2 | C16 | Cl | 8 | 3772 |
| D3ClNC16 | 3 | C16 | Cl | 16 | 7685 |
| D4ClNC16 | 4 | C16 | Cl | 32 | 15511 |
| D3ClNC8 | 3 | C8 | Cl | 16 | 5893 |
| D3ClNC10 | 3 | C10 | Cl | 16 | 6341 |
| D3ClNC14 | 3 | C14 | Cl | 16 | 7237 |
| D3BrNC14 | 3 | C14 | Br | 16 | 7949 |

The antibacterial activity of the dendrimer biocides depends on the generation, n, (size, molecular weight) of the dendrimer, the chain length of the hydrophobe (A, B, and Y) on the quaternary ammonium ion and the counter-anion X. The biocidal activity is in the order of D5ClNC12>D4ClNC12>D1ClNC12>D2ClNC12>D3ClNC12.

High charge density also plays a substantial role in determining antimicrobial properties of polycationic biocides. Since the active species are the cations, different counter-anions can affect antimicrobial properties by influencing disassociation of polycationic biocides in water. D3BrNC14 is more potent than D3ClNC14. While D3ClNC14 is not so effective in killing *E. coli* at 1.8 mM, D3BrNC14 reduces the relative bioluminescence of the bacteria to about 0.2% in 1 hour. The potency difference of dendrimer biocides with chloride and bromide counter-anions was not expected since both these ions tend to dissociate freely in water.

To verify that the antimicrobial effect of the dendrimer biocides is not bacteria dependent, their antibacterial properties against Gram-positive bacteria *Staphylococcus aureus* were investigated by suspension tests. Results show that D4ClNC12 inhibited the growth of *S. aureus* as low as 1 ppm and effectively killed them at 10 ppm in 60 min. Somewhat less effective results have been reported for DTAC. This demonstrates the strong potency of dendritic biocides on typical gram-positive bacteria *S. aureus*.

EXAMPLES

Specific Embodiments of Formula I
Species 1
wherein
  D is a —NH2 terminated polypropylene imine (PPI) dendrimer.
  n=1
  z is substantially equal to $2^{(n+1)}$;
  x is Cl
  R is —CO—NH—CH2—CH2—
  Y is an alkyl of length C12
  A is —CH3.
  B is —CH3
Species 2
wherein
  D is a —NH2 terminated polypropylene imine (PPI) dendrimer.
  n=2
  z is substantially equal to $2^{(n+1)}$;
  x is Cl
  R is —CO—NH—CH2—CH2—
  Y is an alkyl of length C12
  A is —CH3.
  B is —CH3
Species 3
wherein
  D is a —NH2 terminated polypropylene imine (PPI) dendrimer.
  n=3
  z is substantially equal to $2^{(n+1)}$;
  x is Cl
  R is —CO—NH—CH2—CH2—
  Y is an alkyl of length C12
  A is —CH3.
  B is —CH3
Species 4
wherein
  D is a —NH2 terminated polypropylene imine (PPI) dendrimer.
  n=4
  z is substantially equal to $2^{(n+1)}$;
  x is Cl
  R is —CO—NH—CH2—CH2—
  Y is an alkyl of length C12
  A is —CH3.
  B is —CH3
Species 5
wherein
  D is a —NH2 terminated polypropylene imine (PPI) dendrimer.
  n=5
  z is substantially equal to $2^{(n+1)}$;
  x is Cl
  R is —CO—NH—CH2—CH2—
  Y is an allyl of length C12
  A is —CH3.
  B is —CH3
Species 6
wherein
  D is a —NH2 terminated polypropylene imine (PPI) dendrimer.
  n=2
  z is substantially equal to $2^{(n+1)}$;
  x is Cl
  R is —CO—NH—CH2—CH2—
  Y is an alkyl of length C16
  A is —CH3.
  B is —CH3
Species 7
wherein
  D is a —NH2 terminated polypropylene imine (PPI) dendrimer.
  n=3
  z is substantially equal to $2^{(n+1)}$;
  x is Cl
  R is —CO—NH—CH2—CH2—
  Y is an alkyl of length C16
  A is —CH3.
  B is —CH3

Species 8
wherein
  D is a —NH2 terminated polypropylene imine (PPI) dendrimer.
  n=4
  z is substantially equal to $2^{(n+1)}$;
  x is Cl
  R is —CO—NH—CH2—CH2—
  Y is an alkyl of length C 16
  A is —CH3.
  B is —CH3
Species 9
wherein
  D is a —NH2 terminated polypropylene imine (PPI) dendrimer.
  n=3
  z is substantially equal to $2^{(n+1)}$;
  x is Cl
  R is —CO—NH—CH2—CH2—
  Y is an alkyl of length C8
  A is —CH3.
  B is —CH3
Species 10
wherein
  D is a —NH2 terminated polypropylene imine (PPI) dendrimer.
  n=3
  z is substantially equal to $2^{(n+1)}$;
  x is Cl
  R is —CO—NH—CH2—CH2—
  Y is an alkyl of length C10
  A is —CH3.
  B is —CH3
Species 11
wherein
  D is a —NH2 terminated polypropylene imine (PPI) dendrimer.
  n=3
  z is substantially equal to $2^{(n+1)}$;
  x is Cl
  R is —CO—NH—CH2—CH2—
  Y is an alkyl of length C14
  A is —CH3.
  B is —CH3
Species 12
wherein
  D is a —NH2 terminated polypropylene imine (PPI) dendrimer.
  n=3
  z is substantially equal to $2^{(n+1)}$;
  x is Br
  R is —CO—NH—CH2—
  Y is an alkyl of length C14
  A is —CH3.
  B is —CH3

Example I
Synthesis of a Quaternary Ammonium Dendrimer

3–5 grams of DSM Astramol™ polypropylene imine dendrimer are dissolved in 300 ml anhydrous DMAc. A total of 600 ml of anhydrous toluene is divided equally into 3 portions and was used to strip moisture (4–10%) in the dendrimer solution using a rotary evaporator. Because isocyanate chemistry is moisture sensitive, stripping is repeated at least 3 times. A stoichiometic amount of the isocyanate (3–8 grams of 2-chloroethyl isocyanate, or 2-bromoethyl isocyanate) is dissolved in a minimal amount of DMAc (ca. 5 ml) and added dropwise to the dendrimer solution at room temperature. If a significant amount of heat is generated, an ice-water bath is used to prevent side reactions at higher temperatures. The solution is stirred overnight at room temperature. More than a 4-fold excess of tertiary amine is then added in a mixed solvent of DMAc and toluene. The solution is slowly brought up to 80° C. and stirred for 72 hours. The ratio of DMAc vs. toluene was determined empirically. It was noted that the reactants can precipitate during the reaction since the solubility of the products changes a great deal with the percentage of derivitization. In most instances, full derivitization of the dendrimer is the desired end point. After the reaction, quaternary ammonium salts are repeatedly precipitated in large volumes of acetone. These precipitates are extremely hygroscopic. The precipitates are filtered, redissolved in a minimal amount of ethanol, and repeatedly stripped with anhydrous toluene to remove moisture. The samples are dried for ~120 hr at 65° C. in a vacuum oven and stored in a vacuum desiccator. Generally some samples appear to be crystalline while others are amorphous. For the amorphous samples, recrystallization in acetone:methanol (9:1, v/v) improves sample purity. A semi-continuous process called diafiltration, a combination of dialysis and ultrafiltration, is used for further purification. The diafiltration usually takes 2–3 days. The diafiltration may be stopped when the exit stream does not contain any tertiary amine or other small molecules detectable by a gas chromatography-mass spectrometer (GC-MS). The dendrimer biocides are also highly hygroscopic. Therefore, storage in vacuum desiccator is required.

Example II
Characterization

The synthesized quaternary ammonium dendrimers maybe characterized with a variety of techniques. Since dendrimers have the capacity to trap small molecules and quaternary ammonium compounds in general are very hygroscopic, elemental analysis results are typically not reliable.

FTIR experiments of the dendrimer biocides can be conducted in transmission mode. A typical spectrum collected from, for example, species 11, D3ClNC14 shows C—H saturation at 2930.4 cm$^{-1}$, C=O at 1639.9 cm$^{-1}$, N—H bend at 1562.3 cm$^{-1}$ and N—H stretch at 3297.9 cm$^{-1}$. Due to the layer-by-layer structure of the dendrimers and the homologous series of dendrimer biocides, the FTIR spectra of the dendrimer biocides are very similar.

Typical proton and $^{13}$C NMR spectra can be compared with the reagents including generation 2 dendrimer and dimethyl dodecyl amine. The difference of spectra clearly shows the progress of the reaction. The urea proton (CO—NH—CO) were observed at d=6.72 ppm ($^1$H NMR, CDCl$_3$) and the carbonyl carbon (CO—NH—CO) were observed at d=158.7 ($^{13}$C NMR, 15% in CDCl$_3$). Two different carbons in the methyl groups were clearly identified with $^{13}$C NMR. The methyl groups connected directly to nitrogen were observed at 51.1 ppm, while the methyl carbon at the end of the hydrophobic chain was observed at 13.8 ppm. The NMR results also showed approximately complete conversion of the end groups of the dendrimers. The assignment of peaks of $^{13}$C and proton NMR for, for example, species 11, D3ClNC14 D3ClNC12 is shown in Tables IV and V.

The NMR spectra of different dendrimer biocides were also very similar due to the layer-by-layer structure of the dendrimers and similar quaternary ammonium functional groups.

TABLE IV

Assignment of $^{13}C$ peaks for D3ClNC12

| | $^{13}C$ NMR peak |
|---|---|
| NHCONH | 158.67 |
| $CH_3$ | 13.83 |
| $NCH_2C_{10}H_{20}CH_3$ | 22.35–29.27 |
| $NCH_2C_{10}H_{20}CH_3$ | 64.75 |
| $NCH_3$ | 51.09 |
| CH2CH2NC12H25 | 62.95 |
| CH2CH2NC12H25 | 31.56 |
| $CH_2CH_2CH_2NHCONH$ | 31.56 |
| $CH_2CH_2CH_2NHCONH$ | 22.35 |
| $CH_2CH_2CH_2NHCONH$ | 50.95 |
| $NCH_2CH_2CH_2N$ | 50.95 |
| $NCH_2CH_2CH_2N$ | 22.35 |

TABLE V

Assignment of Proton NMR peaks for D3ClNC12

| | Proton NMR peak |
|---|---|
| NHCONH | 7.09, 6.68 |
| $CH_3$ | 0.89 |
| $NCH_2C_{10}H_{20}CH_3$ | 1.25–1.73, 1.82–1.87 |
| $NCH_3$ | 3.36 |
| $CH_2CH_2NC_{12}H_{25}$ | |
| $CH_2CH_2CH_2NHCONH$ | 2.54–3.77 |
| $NCH_2CH_2CH_2N$ | |

Example III
Antimicrobial Properties of the Dendrimer Biocides

A typical laboratory non-slime producing strain of *Staphylococcus aureus* (Newman) was used as a model infection-causing bacterium. The strain was obtained from American Typical Culture Collection (ATCC, Manassas, Va.). *S. aureus* is a pathogenic, Gram-positive bacterium, which typically can be found on human skin. These bacteria are also responsible for implant and medical device centered infections. A typical Gram-negative *E. coli* (ATCC 25922) was also obtained from ATCC. This particular strain was recommended by the U.S. Food and Drug Administration to be used for toxin susceptibility testing. For bioluminescence experiments, several strains of recombinant *E. coli* are used. The recombinant *E. coli* strains containing a fusion of *Escherichia coli* heat shock promoters and a lux gene of *Vibrio fischeri* were developed at DuPont. Relevant information regarding various strains is known to those skilled in the art.

*S. aureus* was maintained on tryptic soy agar plates at 4° C. until required for use. A single colony was transferred to sterile tryptic soy broth and incubated overnight at 37° C. These cells were then centrifuged and washed twice with phosphate buffered saline (PBS, pH 7.4). Approximate cell concentration was determined using a Petroff-Hausser counting chamber (Scientific Products, Edison, N.J.). The bacteria suspensions were then diluted to the test concentration.

*E. coli* stock solutions, kept at −80° C. freezer until required for use, were prepared in Lucia-Barton (LB) media supplemented with 20% glycerol. Glycerol was added to protect bacteria during freezing and thawing processes. During inoculation, a required amount of *E. coli* suspension (typically 10%) was added to fresh and sterile LB broth and incubated overnight at 37° C. These cells were also centrifuged and washed twice with phosphate buffered saline. Cell concentration was determined using a Petroff-Hausser counting chamber (Scientific Products, Edison, N.J.). Bacteria suspensions were then diluted to the test concentration. The recombinant *E. coli* strains were also stocked in a similar way to the wild-type *E. coli*. The medium used was Lucia-Barton (LB) supplemented with 25 mg/ml kanamycin monosulfate to maintain the plasmid. These plasmid-containing strains were grown to an early exponential phase at 30° C. The temperature used was lower than normal because enzymes responsible for generating light would be deactivated at 37° C. These cells were also centrifuged and washed twice with 0.1% peptone water before use.

There are a variety of methods that can be used to evaluate the antimicrobial properties of new materials. Method selection often depends on specific applications. Antimicrobial test results might be reported qualitatively, using terms as sensitive, intermediate, or resistant, or quantitatively in terms of concentration of an agent needed to inhibit or kill bacteria. Suspension tests are typically used to evaluate water-soluble antimicrobials, while surface antimicrobial tests are designed to characterize the antimicrobial properties of non-leaching biocidal materials.

During suspension tests, the effectiveness of biocides was quantified by mixing a suspension of viable bacteria and a certain concentration of test materials and monitoring the subsequent number of live cells at distinct time points. Bacteria were grown overnight and harvested as described. The plate-count method and bioluminescence test methods are two ways to quantify live cells.

In using the plate-count method, cells were re-suspended in a PBS buffer at a concentration between $1 \times 10^8$ and $1 \times 10^9$ cells/ml in sterile, 15-ml polypropylene centrifuge tubes (VWR Scientific Products, West Chester, Pa.). The viable cell concentration was determined by making a series of 10-fold dilutions of the cell suspension and spreading the bacteria on agar plates. The plates were then incubated over night at 30° C. for recombinant *E. coli* and 37° C. for *S. aureus* and wild-type *E. coli*. The visible colonies on the plates were then counted in 24–48 hours. Each colony represents one viable bacterium from the original suspension. The number of colonies, multiplied by the dilution, provides a measure of the viable cells in the original suspension.

In these studies, a dendrimer biocide was added to a cell suspension. The suspension was then agitated thoroughly with a vortexer (Scientific Products, McGraw Park, Ill.). Aliquots of the suspension were removed after 15, 30, and 60 minutes of biocide exposure. The aliquots were immediately used in a series of 10-fold dilutions with buffer containing 10% Tween 80 (Aldrich Chemical Company, Milwaukee, Wis.), which was utilized as a deactivating agent for the quaternized moieties. Without the denaturing agents, test samples would continue to exert its toxic influence, thereby increasing the apparent activity of the biocide.

For the bioluminescence experiments, several strains of recombinant *E. coli* were used. These recombinant *E. coli* strains containing a fusion of *Escherichia coli* heat shock promoters. Whenever bacteria receive stress from a toxic compound, the intensity of light emitted from the bacteria will change. From a "light-on" or "light-off" response one can obtain real-time cell viability data. Strain TV 1048, in which the lux operon is coupled to the promoter of lac operon, was used in this study. Bioluminescence is observed under normal growth conditions. Whenever the bacteria are in a biocidal environment, the light-off response quantitatively corresponds to the antibacterial effect.

During experiments, these plasmid-containing strains were grown to an early exponential phase at 30° C. in LB medium and then incubated with a known amount of the test sample. Bioluminescence was measured either in real time or at some time intervals using a luminometer (Model 20e, Turner Design, CA) and the data were recorded by a computer with data collection capacity.

The antibacterial property of D3ClNC14 against Gram-negative *E. coli* was determined by a bioluminescence method. Bioluminescence is observed under normal growth conditions for the recombinant *E. coli* strain TV 1048. Whenever the bacteria are in a biocidal environment, the light-off response corresponds to the toxic effect of the biocide. The result is expressed as the sample bioluminescence normalized to a control (without biocidal dendrimer of the present invention) vs. time. The reduction of luminescence quantitatively shows the antibacterial activity of the sample. At 4 ppm, the dendrimer biocide inhibited the growth of *E. coli,* but the bacteria could adjust to the environmental stress and survive. At higher concentrations (20 ppm), the bioluminescence decreased very rapidly and went down to undetectable levels in 15 min indicating a strong biocidal effect. In a control experiment, the bioluminescence of the bacteria did not change much (5%) if the same concentration of pure PPI generation 3 dendrimers was added.

To quantify the level of the biocidal effect of the cationic dendrimer and to compare it to their small molecule counterpart, n-dodecyltrimethyl ammonium chloride (DTAC), EC50was determined. $EC_{50}$ is defined as the concentration of the compound, which causes a 50% reduction of the bioluminescence in a certain time period. $EC_{50}$ concentrations were determined by interpolation of the bioluminescence against concentration curves at a specific time. A lower $EC_{50}$ indicates a more toxic compound. $EC_{50}$ of, for example, species 3, D3ClNC12 is about 12 ppm at 5 min, while $EC_{50}$ of DTAC is about 2000 ppm at 5 min. The dendrimer architecture increases the potency of DTAC against *E. coli* over 100 times.

Example IV
The Preparation of Immobilized Dendrimers on Polyurethanes

A typical synthesis procedure preparation of immobilized dendrimers on polyurethanes is described as follows. 10 grams of polyurethane are dissolved in 200 ml of DMAc. The solution is repeatedly stripped with 1000 ml of toluene to reduce moisture content. The solution is then put into a salt-ice bath (−15° C.) to cool down to around −5° C. A calculated amount of sodium hydride (ca. 25–40 mg) is washed with anhydrous toluene and added into the polyurethane solution. The solution is then stirred for about 30 min until a greenish/yellow color of urethane negative ion appears. A dry DMAc solution (10–20 ml) of dendrimer biocide (1–2 g) is added dropwise to the activated polyurethane solution. The salt-ice bath was then removed and the solution is stirred at room temperature overnight. The polyurethane is precipitated into a large amount of ethanol (ca. 1000 ml). The precipitate is extensively washed with a large volume of ethanol to remove unreacted dendrimer biocide. The sample is then dried in a vacuum oven for 48 hr at 60° C.

All publications and patents mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in dendrimers, synthetic organic chemistry, antimicrobial compositions and formulations or related fields are intended to be within the scope of the following claims.

What is claimed is:

1. A quaternary ammonium functionalized dendrimer of the formula:

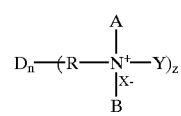

(Formula I)

wherein
D is a dendrimer;
n is the generation number of the functionalized dendrimer selected from the group consisting of 1, 2, 3, 4, 5, 6, 7, 8, 9, 10, 11, 12, 13, 14, and 15;
z is an integer less than or equal to $2^{(n+1)}$;
x is an anion;
R is a linking group;
Y is an alkyl group having 1 to 32 carbon atoms, an aryl group having 1 to 32 carbon atoms, or chloromethyl;
A is an alkyl group having 1 to 32 carbon atoms, an aryl group having 1 to 32 carbon atoms, or chloromethyl; and
B is an alkyl group having 1 to 32 carbon atoms, an aryl group having 1 to 32 carbon atoms, or chloromethyl.

2. A quaternary ammonium functionalized dendrimer according to claim 1 wherein D is selected from the group consisting essentially of polyamidoamine dendrimers, polylysine based dendrimers, polyethylene oxide based dendrimers, silicon based dendrimers, polypropylene imine dendrimers, polyether based dendrimers, polyethylene oxide based hyperbranched polymers, polyglycerol based hyperbranched polymers, silicon based hyperbranched polymers, hyperbranched polyols and hybrane.

3. A quaternary ammonium functionalized dendrimer according to claim 2 wherein n is selected from the group consisting of 1, 2, 3, 4, 5, and 6.

4. A quaternary ammonium functionalized dendrimer according to claim 2 wherein x is selected from the group of anions consisting essentially of chloride, bromide, sulfate, nitrate, chlorate, tetrafluoroborate, perchlorate, hexafluorophosphate, permanganate, and sulfite.

5. A quaternary ammonium functionalized dendrimer according to claim 4 wherein linking group R is selected from the group consisting essentially of —CO—NH—CH2—CH2—, —CO—NH—CH2—, —CO—NH—CH2—CH2—CH2—, —CO—NH—CH2—CH2—CH2—CH2, —CO—NH—CH2—CH2—CH2—CH2—CH2—, —CO—NH-Phenyl-CH2—, —CO—NH—CH2—CH2—O—CH2—CH2—, —(CH2)—, —(CH2)$_2$—, —(CH2)$_3$—, —(CH2)$_4$—, —(CH2)$_5$—, —(CH2)$_6$—, —(CH2)$_7$—, —(CH2)$_8$—, —(CH2)$_9$—, (CH2)$_{10}$—, —(CH2)$_{11}$—, —(CH)2)$_{12}$—, —(CH2)$_{13}$—, —(CH2)$_{14}$—, —(CH2)$_{15}$—, —(CH2)$_{16}$—, —(CH2)$_{17}$—, —(CH2)$_{18}$—, —(CH2)$_{19}$—, and —(CH2)$_{20}$—.

6. A quaternary ammonium functionalized dendrimer according to claim 5 wherein Y is an alkyl having 1 to 30 carbon atoms.

7. A quaternary ammonium functionalized dendrimer according to claim 6 wherein Y is a linear alkyl group having 8 to 24 carbon atoms. group consisting of within the range of 1 to 30 carbon atoms.

8. A quaternary ammonium functionalized dendrimer according to claim 5 wherein Y is an aryl group selected from the group consisting essentially of phenyl, —(CH2)-phenyl, —(CH2)$_2$-phenyl, —(CH2)$_3$-phenyl, —(CH2)$_4$-phenyl, —(CH2)$_5$-phenyl, —(CH2)$_6$-phenyl, —(CH2)$_7$-phenyl, —(CH2)$_8$-phenyl, —(CH2)$_9$-phenyl, (CH2)$_{10}$-phenyl, —(CH2)$_{11}$-phenyl, —(CH2)$_{12}$-phenyl, —(CH2)$_{13}$-phenyl, —(CH2)$_{14}$-phenyl, —(CH2)$_{15}$-phenyl, —(CH2)$_{16}$-phenyl, —(CH2)$_{17}$-phenyl, —(CH2)$_{18}$-phenyl, —(CH2)$_{19}$-phenyl, —(CH2)$_{20}$-phenyl, —(CH2)$_{21}$-phenyl, —(CH2)$_{22}$-phenyl, —(CH2)$_{23}$-phenyl, and —(CH2)$_{24}$-phenyl.

9. A quaternary ammonium functionalized dendrimer according to claim 5 wherein Y is chloromethyl.

10. A quaternary ammonium functionalized dendrimer according to claim 5 wherein A and B are alkyl groups, the same or different, each having 1 to 30 carbon atoms.

11. A quaternary ammonium functionalized dendrimer according to claim 10 wherein A and B are linear alkyl groups, the same or different, each having 1 to 24 carbon atoms.

12. A quaternary ammonium functionalized dendrimer according to claim 5 wherein A and/or B is an aryl group selected from the group consisting essentially of phenyl, —(CH2)-phenyl, —(CH2)$_2$-phenyl, —(CH2)$_3$-phenyl, —(CH2)$_4$-phenyl, —(CH2)$_5$-phenyl, —(CH2)$_6$-phenyl, —(CH2)$_7$-phenyl, —(CH2)$_8$-phenyl, —(CH2)$_9$-phenyl, (CH2)$_{10}$-phenyl, —(CH2)$_{11}$-phenyl, —(CH2)$_{12}$-phenyl, —(CH2)$_{13}$-phenyl, —(CH2)$_{14}$-phenyl, —(CH2)$_{15}$-phenyl, —(CH2)$_{16}$-phenyl, —(CH2)$_{17}$-phenyl, —(CH2)$_{18}$-phenyl, —(CH2)$_{19}$-phenyl, —(CH2)$_{20}$-phenyl, —(CH2)$_{21}$-phenyl, —(CH2)$_{22}$-phenyl, —(CH2)$_{23}$-phenyl, and —(CH2)$_{24}$-phenyl.

13. A quaternary ammonium functionalized dendrimer according to claim 5 wherein A and/or B is chloromethyl.

14. A quaternary ammonium functionalized dendrimer of Formula I wherein D is an NH2 terminated polypropylene imine (PPI) dendrimer.

15. A quaternary ammonium functionalized dendrimer according to claim 14 wherein n is selected from the group consisting of 1, 2, 3, 4, 5, and 6.

16. A quaternary ammonium functionalized dendrimer according to claim 15 wherein R is —CO—NH—CH2—CH2— and x is Chloride; or R is —CO—NH—CH2— and x is Bromide.

17. A quaternary ammonium functionalized dendrimer according to claim 16 wherein Y is a linear alkyl group having 8 to 24 carbon atoms.

18. A quaternary ammonium functionalized dendrimer according to claim 17 wherein A and B are each —CH3.

19. A method of controlling the growth of a microorganism comprising:
exposing said microorganism to a quaternary ammonium functionalized dendrimer of formula I wherein
D is a dendrimer;
n is the generation number of the functionalized dendrimer selected from the group consisting of 1, 2, 3, 4, 5, 6, 7, 8, 9, 10, 11, 12, 13, 14, and 15;
z is an integer less than or equal to $2^{(n+1)}$;
x is an anion;
R is a linking group;
Y is an alkyl group having 1 to 32 carbon atoms, an aryl group having 1 to 32 carbon atoms, or chloromethyl;
A is an alkyl group having 1 to 32 carbon atoms, an aryl group having 1 to 32 carbon atoms, or chloromethyl; and
B is an alkyl group having 1 to 32 carbon atoms, an aryl group having 1 to 32 carbon atoms, or chloromethyl.

20. A method of controlling the growth of a microorganisms according to claim 19 wherein said microorganism is selected from the group consisting essentially of acidogenic gram-positive cocci, Gram-negative anaerobic oral bacteria, Group A streptococci, enteric bacteria, Gram-negative rods, and Gram-positive cocci.

21. A method of controlling the growth of a microorganisms according to claim 20 wherein said microorganism is selected from the group consisting essentially of streptococcus, staphylococci, *haemophilus influenzae, escherichia coli, P. aeruginosa, burkholderia cepacia, Pseudomonas pseudomallei, C. albicansm, staphylococcus epidennidis,* and *S. aureus.*

22. A method of controlling the growth of a microorganism according to claim 19 wherein said microorganism is a spore.

23. A method of controlling the growth of a microorganism according to claim 22 wherein said spore corresponds to *B. anthracis* or anthrax.

24. A method of controlling the growth of a microorganism according to claim 19 wherein said quaternary ammonium functionalized dendrimer is immobilized on a surface.

25. A method of controlling the growth of a microorganism according to claim 24 wherein said surface is comprised of a polymer, or glass, or metal.

26. A method of controlling the growth of a microorganism according to claim 25 wherein said surface polymer is selected from the group consisting of polyurethane, polystyrene, polyethylene, and polypropylene.

27. A method of controlling the growth of a microorganism according to claim 19 wherein said quaternary ammonium functionalized dendrimer is applied as a spray.

28. A method of controlling the growth of a microorganism according to claim 19 wherein said quaternary ammonium functionalized dendrimer is incorporated into a coating.

* * * * *

UNITED STATES PATENT AND TRADEMARK OFFICE
CERTIFICATE OF CORRECTION

PATENT NO. : 6,440,405 B1
DATED : August 27, 2002
INVENTOR(S) : Cooper et al.

It is certified that error appears in the above-identified patent and that said Letters Patent is hereby corrected as shown below:

Column 21,
Line 6-7, delete "group consisting of within the range of 1 to 30 carbon atoms."

Signed and Sealed this

Twenty-sixth Day of November, 2002

Attest:

Attesting Officer

JAMES E. ROGAN
Director of the United States Patent and Trademark Office